(12) United States Patent
Bondon

(10) Patent No.: US 12,128,121 B2
(45) Date of Patent: Oct. 29, 2024

(54) COMPOSITIONS COMPRISING ORGANO-SILANOL COMPOUNDS, AND APPLICATIONS

(71) Applicant: EXSYMOL, Monaco (MC)

(72) Inventor: Pierre Bondon, Monaco (MC)

(73) Assignee: EXSYMOL, Monaco (MC)

( * ) Notice: Subject to any disclaimer, the term of this patent is extended or adjusted under 35 U.S.C. 154(b) by 0 days.

(21) Appl. No.: 17/999,321

(22) PCT Filed: May 20, 2021

(86) PCT No.: PCT/EP2021/063565
§ 371 (c)(1),
(2) Date: Nov. 18, 2022

(87) PCT Pub. No.: WO2021/234130
PCT Pub. Date: Nov. 25, 2021

(65) Prior Publication Data
US 2023/0181444 A1    Jun. 15, 2023

(30) Foreign Application Priority Data

May 20, 2020 (FR) .................................. FR2005373

(51) Int. Cl.
| | | |
|---|---|---|
| A61K 8/58 | (2006.01) | |
| A61K 31/695 | (2006.01) | |
| A61Q 19/08 | (2006.01) | |
| C07F 7/18 | (2006.01) | |

(52) U.S. Cl.
CPC ............ *A61K 8/585* (2013.01); *A61K 31/695* (2013.01); *A61Q 19/08* (2013.01); *C07F 7/1876* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 3,364,246 | A  * | 1/1968 | Rossmy ................ | A61K 8/892 556/415 |
| 5,037,803 | A | 8/1991 | Gueyne et al. | |
| 6,197,986 | B1 * | 3/2001 | Seguin ..................... | A61K 8/60 556/404 |
| 2002/0006383 | A1 * | 1/2002 | Anderson ............... | A61K 8/55 424/401 |
| 2003/0170198 | A1 * | 9/2003 | Williams ............. | A61K 8/9794 424/73 |
| 2004/0162231 | A1 * | 8/2004 | Hagino .................. | A61Q 19/00 424/195.17 |
| 2007/0031355 | A1 * | 2/2007 | Fonolla Moreno ...... | A61K 8/26 424/59 |
| 2010/0113385 | A1 * | 5/2010 | Seguin .................. | C07F 7/0836 536/55.1 |
| 2011/0061567 | A1 | 3/2011 | Masatoshi et al. | |
| 2012/0087882 | A1 * | 4/2012 | Fevola ..................... | A61Q 5/12 514/452 |

FOREIGN PATENT DOCUMENTS

| | | | |
|---|---|---|---|
| FR | 2 230 376 | A1 | 12/1974 |
| FR | 2 897 532 | A1 | 8/2007 |

OTHER PUBLICATIONS

WIPO Application No. PCT/EP2021/063565, PCT International Search Report and Written Opinion of the International Searching Authority mailed Aug. 13, 2021.
WIPO Application No. PCT/EP2021/063565, PCT International Preliminary Report on Patentability mailed Dec. 1, 2022.

\* cited by examiner

*Primary Examiner* — Katherine Peebles
(74) *Attorney, Agent, or Firm* — Alston & Bird LLP

(57) ABSTRACT

A composition comprising stabilised organo-silanol compounds, said composition comprising two different organo-silanols and an organo-silanol(s) stabilising/complexing agent.

13 Claims, No Drawings

COMPOSITIONS COMPRISING ORGANO-SILANOL COMPOUNDS, AND APPLICATIONS

CROSS-REFERENCE TO RELATED APPLICATIONS

This application is a national stage entry of International Application No. PCT/EP2021/063565 filed May 20, 2021, which claims the benefit of FR Application No. FR2005373 filed May 20, 2020, each of which is hereby incorporated by reference.

FIELD OF THE INVENTION

The present invention relates to the field of compositions comprising stabilised and bioavailable organo-silanol compounds, as well as their applications.

STATE OF THE ART

Among the chemical elements identified in the Earth's crust, the solid part of the Earth's surface, silicon ranks second after oxygen with almost 28% of its composition by mass. However, this metalloid does not appear in the free and elementary state of a pure substance. Indeed due to the very strong reactivity between the two elements, silicon combines with ambient oxygen to generate a multitude of oxides, such as the highly abundant silica (silicon dioxide, [$SiO_2$]), as well as various tetrahedral structures [$SiO_4^{4-}$] collectively known as "silicates" which are polymerised and/or associated with one or more alkali or metal cations (Martin K. R., Met. Ions Life Sci., 2013, vol. 13, pp. 451-473). Thus, the element silicon in such multi-atomic forms, usually solid and having a crystalline or amorphous state, insoluble in water, turns out to be present everywhere in the Earth's soils, notably in many rocks as common as sandstone, granite, clay, sand, etc. Furthermore, more than 90% by weight of the mineral landscape of the Earth's crust is reportedly composed of such siliceous structures, collectively known in this case by the generic term of "lithogenic silica" (R. Jugdaohsingh, J. Nutr. Health Aging, 2007, vol. 11, pp. 99-110). With such a geology, natural water, both surface and well water, also presents silicon in its composition, in several different water-soluble forms collectively designated by another term, "silicic acid", to combine the monomeric form represented by orthosilicic acid [$H_4SiO_4$] and hydrated oligomeric forms which are mainly meta- [$H_2SiO_3$], di- [$H_2Si_2O_5$] and tri-silicic acids [$H_2Si_3O_7$] (Martin K. R., J. Nutr. Health Aging, 2007, vol. 11, pp. 94-9; Jurkić L. M. et al, Nutr. Meta. 2013, vol. 10, pp. 1-12).

In living matter, in contrast to the mineral kingdom, the general prevalence of silicon is comparatively less marked. For example, only a few living unicellular organisms present in the seabed are able to accumulate silicon in the form of a "biogenic silica", a fraction of particulate silica which they manufacture themselves, notably for the purpose of ensuring the robustness of the living cell, in particular with respect to predators, and of protecting themselves from ultraviolet radiation. Diatoms, unicellular planktonic organisms often associated with microalgae, constitute the best known example thereof with an endoskeleton, or frustule, which is actually siliceous (Rabovsky J., Scand. J. Work Environ. Health, 1995, vol. 21, pp. 108-110). Plants also absorb and concentrate silicon from silicon-containing soils and waters, for the purposes of growth and resistance to the abiotic stresses to which they are exposed (climate variations, heavy metals, etc.) and in the form of "colloidal silica", i.e. a suspension of fine silica particles and at concentrations that vary between the plant species, their genotype, the plant phenophase, the season, the nature of the soil, etc. (Currie H. A. et al., Ann. Botan, 2007, vol. 100, pp. 1383-1389 and references cited). Finally with regard to humans, they are born with a silicon capital which amounts to the third most abundant trace element in the human body after iron and zinc. In an adult's body, the amount of silicon varies between a mass of 1 and 2 grams, with a ubiquitous presence in biological tissues and fluids (Gotz W. et al., Pharmaceutics, 2019, vol. 11, pp. 1-27). Even if it is only a trace element, and therefore by definition a substance present in the body in very small quantities exclusively through nutrient intake (the body cannot manufacture it), the active involvement of silicon in the physiology of the human body no longer requires demonstration, with benefits in mechanisms as varied as bone mineralisation and osteoporosis prevention, stimulation of protein fibre production (collagen, elastin) and prevention of skin and appendage ageing, reduced risks of atherosclerosis, of Alzheimer's disease, combating blood pressure disorders, oxidative stress, inflammation, etc. (Martin K. R., Met. Ions Life Sci, 2013, vol. 13, pp. 451-473 and references cited). It plays in particular a predominant role in maintaining the structural and metabolic integrity of the connective and supporting tissues that give shape and support to the body, mainly all tissues that require strength and flexibility, such as those found in muscles, skin, bones, cartilages, joints, tendons, ligaments, arteries (Vasanthi N. et al., World Appl. Sci. J., 2012, vol. 17, pp. 1425-1440).

However, on the one hand, silicon capital in humans decreases naturally and irreversibly with age from sexual maturity (Bissé E. et al., Annal Biochem, 2005, vol. 337, pp. 130-135). On the other hand, the daily diet and consumption of foods and beverages renowned for their silicon content (wholegrain cereals, green beans, bananas, beer, etc.) struggle to offset this depletion, due to ingested silicon not being entirely in a form directly assimilable by the gastrointestinal tract, and the body's inability to store any potential surplus. Finally, as is well-known in silicon chemistry, the only natural form of a truly assimilable and bioavailable silicon, represented by orthosilicic acid [$Si(OH)_4$], unfavourably displays a low concentration in water (<2 mM or 56 mg Si/l) due to a very high tendency to self-condense as silicon levels rise, consequently producing polymerised forms (in particular via the establishment of intermolecular siloxane bonds (Si—O—Si) between the silanol functions (Si—OH) carried by the orthosilicic acid molecules) whose absorbability is low or harder for the body and are therefore potentially inert or with low biological activity (Jurkic L. M. et al, Nutr. Meta. 2013, vol. 10, pp. 1-12). In order to remedy such obstacles and difficulties of silicon assimilation, a remarkable scientific advance was, at the end of the 1950s, the object of patents FR1234213 and FR1069 and intended for therapeutic use, the creation through organic synthesis of an "organic silicon", so called because its presented structure, in contrast to mineral silicon, of a silicon atom bound for the first time to a carbon atom. Behind this rather mundane expression the aim was for a silicon derivative which, in comparison with the natural form, orthosilicic acid, displays much better behaviour in water (~21 mM or 588 mg Si/l for [$CH_3$—$Si(OH)_3$]), which is assimilable, stable, and structurally of the "organo-silicic complex" type, as per the titles of the above-mentioned patents. Chronologically, the first "organic silicon" thus conceived was in the form of the monomethylsilanetriol monomer molecule

[CH₃—Si(OH)₃] stabilised by salicylic acid, also historically described as "first generation organic silicon". Other versions followed, with, for example some time later, the development of a "second generation organic silicon", in which citric acid replaced salicylic acid due to patients allergic to salicylate derivatives (https://laurepouliquen.fr/quest-ce-que-le-silicium-organique/ & "L'aventure du silicium organique" Ambre Editions, 2010). In any event, throughout the decades following these initial developments, the state of the art has been regularly enriched with new versions or "generations" of stabilised and assimilable organic silicon, even if the claimed purposes have moved away from the original therapeutic use. As an illustration of this aspect, we can mention for example the "cosmetic silicons" which were the object of patent EP0289366, which, according to the inventors of said patent, consist of hydroxysilane-type molecular complexes intended to constitute new products for skincare or haircare application, characterised by a double-carrying silicon atom, and a specific biologically active compound, and a macromolecule (hydrolysed elastin, etc.) with a "dermatophilic" character and with the original action of fixing organic silicon at the intra-cutaneous level and thus preventing its passage into the underlying skin tissues. We can also mention studies carried out by the applicant with the design of complexes based on biologically active organo-silicon compounds in the original form of a powder in order to be able to integrate non-aqueous cosmetic and pharmaceutical presentations (tablets, pills) that can be administered orally (patent EP0867445). Closer to us, we can also mention, in response to a specific skin problem, the design in an aqueous medium of new complexes capable of providing the skin with a biologically active silicon, consisting of an organo-silanol entity, preferably methylsilanetriol, associated and stabilised by weak bonds (hydrogen bonds) with original substances such as calibrated fragments of a glycosaminoglycan (patent EP2172186) or even a selection of monomeric deoxy-sugars (patent FR3038898). Finally, we can also mention two other examples from the recent literature, which moreover evidences the constant interest that organic silicon still induces, as it has done since its creation. The first of these, which is the object of the international application WO2018/037115, concerns a composition presented as being highly concentrated in a bioavailable, highly assimilable silicon complex, stable at an alkaline pH and combining in the aqueous phase a monomeric organosilanolate, preferably monomethylsilanolate, with at least one chelating agent. The second, which is the object of an article, concerns a methylsilanetriol associated and stabilised by hydrogen bonds with two substances of structural interest for their phenolic units. The stability and bioavailability for cosmetic purposes of the complexes thus obtained are particularly underlined therein (Fastré M. et al., 2018, Chem. Sci. J., vol. 9, pp. 1-3).

However, it turns out to be essential to design and develop, over and over, new versions/"generations" of organic silicon, more stable, bioavailable and biologically active (in particular by minimising the risk of self-condensation and production of polymerised and water-insoluble forms via the establishment of intermolecular siloxane bonds(Si—O—Si), as stated above). The present invention falls within this search for new versions/generations of organic silicon, which are ever more stable, bioavailable and biologically active, in particular for use in cosmetic and/or dermocosmetic and/or drinkable nutricosmetic formulations. In particular, one of the objectives sought by the applicant was to develop, in a polar solvent, an alternative and improved generation of an organic silicon having notably a very high stability over time and being highly bioavailable and biologically active (in particular on the skin including to its deepest layers).

DESCRIPTION OF THE INVENTION

In such a research context aiming at developing a new generation of organic silicon meeting the above-mentioned requirements, the applicant set out to improve complexes or compositions comprising an organo-silanol associated with one or more stabilising/complexing agents. However, and in a break with the traditionally followed approach, instead of focusing its research on selecting organo-silanol stabilising/complexing agent(s), the applicant worked on the solvolysis of organo-silanols per se, and more precisely on those corresponding to the following general formula (I): X—Si(OH)₃ (I) (wherein the radical X is a linear or branched $C_1$-$C_4$ alkyl group, preferably $C_1$-$C_2$, possibly substituted with at least one hydroxyl group), and in particular on methylsilanetriol, with the aim in particular of increasing the stability of the systems comprising these stabilised organo-silanols (by means of the above-mentioned stabilising/complexing agent(s)). Thus, in the context of its research on the method of preparing in an aqueous medium said organo-silanols of general formula (I), in particular methylsilanetriol, the applicant discovered, against all expectations, that with the introduction of a glycolic solvent of general formula HO—CH($R_1$)—CH($R_2$)($R_3$)(II) (wherein $R_1$ is —H or —CH₃; $R_2$ is —H, —OH, or —CH₃; $R_3$ is —CH₃, —CH₂—CH₃, —CH₂OH, —CH(CH₃)OH, —CH₂—CH₂—CH₃, —CH₂—CH₂—CH₂—CH₃, —CH₂—CH₂—CH₂—CH₂—OH, or —C(CH₃)—OH), the conversion of a fraction of the organo-silanol of general formula (I), as defined above, was observed into another organo-silanol of following general formula (III):

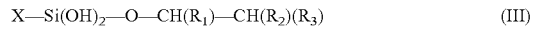

X—Si(OH)₂—O—CH($R_1$)—CH($R_2$)($R_3$)    (III)

wherein:
the radical X is a linear or branched $C_1$-$C_4$ alkyl group, preferably $C_1$-$C_2$, possibly substituted with at least one hydroxyl group (preferably with one hydroxyl group), with X preferably being a methyl group
$R_1$ is —H or —CH₃;
$R_2$ is —H, —OH, or —CH₃;
$R_3$ is —CH₃, —CH₂—CH₃, —CH₂OH, —CH(CH₃)OH, —CH₂—CH₂—CH₃, —CH₂—CH₂—CH₂—CH₃, —CH₂—CH₂—CH₂—CH₂—OH, or —C(CH₃)(CH₃)—OH.

The above-mentioned conversion is carried out via a mono-alkoxylation reaction between the selected glycolic solvent and one of the hydroxyl groups (carried by the silicon atom) of the organo-silanol of general formula (I), as defined above.

This conversion of a fraction of the organo-silanol of general formula (I) into an organo-silanol of general formula (III) results in the coexistence of organo-silanols of general formulae (I) and (III). Furthermore, and advantageously within the organo-silanol of general formula (III), the occurrence of a strong chemical bond, in this case an —Si—O—C— covalent bond, is observed, a chemically stabilising factor that differentiates it from the organo-silanol of general formula (I) stabilised by hydrogen bonds, as in the prior art. By way of illustration, if methylsilanetriol is specifically considered as an organo-silanol of general formula (I) and 1,3-propanediol considered as a glycolic solvent of general formula (II), the conversion of a fraction of a methylsilanetriol into (3-hydroxypropoxy)-(methyl)silanediol is observed in the presence of said 1,3-propanediol; one of the silanol functions of the methylsilanetriol precursor being stabilised within the (3-hydroxypropoxy)-(methyl)silanediol compound, not by a hydrogen bond as in the prior art, but rather by the formation of an —Si—O—C— covalent bond, resulting from a mono-alkoxylation reaction between the 1,3-propanediol and one of the hydroxyl groups carried by the silicon atom of the methylsilanetriol.

Particularly advantageously, in the presence of one or more stabilising/complexing agents (allowing the stabilisation of the silanol functions via the establishment of hydrogen bond(s) between them and the stabilising/complexing agent(s)), it is possible to observe, in a completely innovative manner, under appropriate operating conditions (determinable by a person skilled in the art, without excessive difficulty, on the basis of the lessons from the present patent application, supplemented, if appropriate, by their general knowledge):

i) a duality of stabilising chemical interactions, essential for the stabilisation of the silanol functions of the organo-silanol of general formula (I), with precisely a concomitant presence of weak bonds (in this case hydrogen bonds) with the stabilising/complexing agent(s) and strong bonds (—Si—O—C— covalent bonds, as stated above), and ii) the formation of a stabilised ternary complex between the organo-silanol of general formula (I), the stabilising/complexing agent(s) and the organo-silanol of general formula (III), which can be represented schematically by:

where:
"OS(I)" refers to the organo-silanol of general formula (I) as defined previously,
"AS" refers to the organo-silanol stabilising/complexing agent(s), as defined previously,
"OS(III)" refers to the organo-silanol of general formula (III) as defined previously, and
the dashed lines represent at least one hydrogen bond.

The findings made by the applicant allowed the design and development of a "new generation organic silicon complex", echoing the "first and second generation organic silicon" mentioned in the preamble, or even the design and development of an "organic silicon hybrid complex".

The object of the invention is therefore a composition, preferably in liquid form, advantageously in the form of a solution, comprising:

a) a first organo-silanol of the following general formula (I):

wherein the radical X is a linear or branched (advantageously linear) $C_1$-$C_4$ alkyl group, preferably $C_1$-$C_2$, possibly substituted with at least one hydroxyl group (preferably with one hydroxyl group), with X preferably being a methyl group;

b) a second organo-silanol of the following general formula (III):

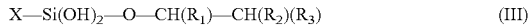

wherein:
the radical X is a linear or branched $C_1$-$C_4$ alkyl group advantageously linear), preferably $C_1$-$C_2$, possibly substituted with at least one hydroxyl group (preferably with one hydroxyl group), with X preferably being a methyl group;

$R_1$ is —H or —$CH_3$;
$R_2$ is —H, —OH, or —$CH_3$;
$R_3$ is —$CH_3$, —$CH_2$—$CH_3$, —$CH_2OH$, —$CH(CH_3)$OH, —$CH_2$—$CH_2$—$CH_3$, —$CH_2$—$CH_2$—$CH_2$—$CH_3$, —$CH_2$—$CH_2$—$CH_2$—$CH_2$—OH, or —$C(CH_3)(CH_3)$—OH; and, c) an organo-silanol(s) stabilising/complexing agent, suitable to allow the formation of a (stabilising) molecular complex with at least one organo-silanol via the establishment of at least one weak chemical bond, preferably at least one hydrogen bond, with the said at least one organo-silanol.

Indeed, notably due to the particularly advantageous technical effects i) and ii) mentioned above, the composition according to the invention presents an organic silicon with notably a very high stability over time, which is bioavailable and biologically active (in particular on the skin).

According to one embodiment, the molar ratio between said first organo-silanol and said second organo-silanol is between 100/1 and 100/20, preferably between 100/10 and 100/15.

According to a preferred embodiment, the composition according to the invention is a hydroglycolic solution, namely comprising a mixture of water and at least one glycolic solvent. Indeed, this hydroglycolic solution represents an optimal environment for allowing the conversion of a fraction of the organo-silanol of general formula (I) into the organo-silanol of general formula (III), via a mono-alkoxylation reaction between the selected glycolic solvent and one of the hydroxyl groups (carried by the silicon atom) of the organo-silanol of general formula (I), leading in situ to the spontaneous formation of a new organosilanol, in chemical equilibrium with the coexisting organo-silanol of general formula (I).

Indeed and in the case for instance of methylsilanetriol, the applicant unexpectedly discovered, during a $^{29}$Si NMR spectroscopy analysis of a stabilised methylsilanetriol introduced in hydroglycolic solution (an analysis carried out for the purpose of ensuring, notably, its predominantly monomer quality):

the creation of an —Si—O—C— covalent bond resulting from a mono-alkoxylation reaction between the selected glycol (in this case, 1,3-propanediol was primarily chosen) and one of the hydroxyls carried by the silicon atom of methylsilanetriol (the latter however expected by the applicant exclusively in the form of a complex stabilised by hydrogen bonds), in order to lead in situ to the spontaneous formation, in chemical equilibrium with coexisting methylsilanetriol, of a new chemical species;

the resulting formation, as this new siliceous chemical species, of the compound "(3-hydroxypropoxy)-(methyl)silanediol" in the case of the above-mentioned methylsilanetriol and 1,3-propanediol.

Regarding this new compound "(3-hydroxypropoxy)-(methyl)silanediol", the applicant points out that it is so named by the standardized naming system for chemical compounds (IUPAC nomenclature). Structurally, it is represented by the following semi-developed chemical formula: $CH_3$—$Si(OH)_2$—O—$CH_2$—$CH_2$—$CH_2$—OH. Finally, its identification in hydroglycolic solution resulted from the following spectral analysis: on the one hand, said new compound carrying said new —Si—O—C— covalent bond is characterised, on the $^{29}$Si NMR control spectrum of the hydroglycolic solution, by the presence of a singlet, clear and above all unprecedented with a chemical shift of minus 39.1 ($\delta$=−39.1 ppm), whereas on the same spectrum, as expected by the applicant, there is another singlet of higher intensity, with a distinct chemical shift of minus 38.6 ppm (δ=−38.6 ppm), corresponding to a methylsilanetriol "traditionally" stabilised by weak interactions (in this case by hydrogen bonds) with the stabilising/complexing agent used, in this case the adenosine (or xylosyladenine) molecule [see test 1 below and method of preparation]. On the other hand, and with regard to the lessons provided by spectral data from the state-of-the-art (Sugahara Y. et al., J. Non-Cryst. Solids, 1994, vol. 167, pp. 21-28), the difference in chemical shift between the two singlets (Δδ=0.5 ppm) is attributable to the formation of the new —Si—O—C— covalent bond.

In addition, such a glycolic solvent has the advantage of being miscible with water, which represents a satisfactory solution to the objective of producing an alternative (and improved) version of stabilised organic silicon, including with stabilising/complexing agents that display rather contrary characteristics: insufficient water solubility, etc. This represents a significant advantage insofar as, as stated in the preamble of the present application, one of the objectives of the present invention is to develop, in a polar solvent (water/glycolic solvent for example), an alternative and improved generation of an organic silicon, in particular having a very high stability over time, which is bioavailable and biologically active (particularly on the skin).

Moreover, such a reaction behaviour of organic silicon, in particular of organo-silanol of general formula (I), in hydroglycolic solution in compliance with controlled conditions (determinable by a person skilled in the art, without excessive difficulty, on the basis of the lessons of the present patent application, supplemented, if appropriate, by their general knowledge) proved to be particularly advantageous and promising in the context of the present invention, notably with regard to the advantageous properties exhibited by such an organic silicon in hydroglycolic solution, illustrated by:
- an ability to display an improved permeability constant, in accordance with a silicon bioavailable and biologically active as far as the deepest layers of the epidermis [see test 2 below];
- an ability to present a very high stability over time in accordance with one of the objectives stated above [see test 3 below];
- an ability to present biologically a cytostimulant activity [see test 4 below];
- an ability to protect cells present in the epidermis and dermis from a cytotoxic and oxidative state induced by a stress situation [see test 5 below];
- an ability to limit the production of a lipid mediator involved in the skin's response to a stressful situation [see test 6 below].

Another interest is that certain glycols, such as propylene glycol in the cosmetics industry, are now exploited as organic solvents and humectants but also for their antimicrobial properties which give them the status of substitutes for certain regulated preservatives whose safety has been called into question in recent years (parabens, etc.).

According to a preferred embodiment of the invention, said at least one glycolic solvent corresponds to the following general formula (II):

wherein:
R$_1$ is —H or —CH$_3$;
R$_2$ is —H, —OH, or —CH$_3$;

R$_3$ is —CH$_3$, —CH$_2$—CH$_3$, —CH$_2$OH, —CH(CH$_3$)OH, —CH$_2$—CH$_2$—CH$_3$, —CH$_2$—CH$_2$—CH$_2$—CH$_3$, —CH$_2$—CH$_2$—CH$_2$—CH$_2$—OH, or —C(CH$_3$)(CH$_3$)—OH.

According to a particular embodiment, said at least one glycolic solvent has the following general formula (IV):

wherein:
the radical R is a hydrogen atom or a C$_1$-C$_4$ alkyl group, notably a C$_1$-C$_2$ alkyl group, preferably a hydrogen atom; and
n is a natural integer between 1 and 4, preferably between 1 and 3, with preferably n being 2.

According to another particular embodiment, said at least one glycolic solvent is selected from 1,2-propanediol, 1,3-propanediol, 1,2-butanediol, 1,3-butanediol, 2-methyl-1,3-propanediol, 1,2,3-propanetriol, 1,2-hexanediol, 1,6-hexanediol, 1,2-dihydroxypentane, hexylene glycol, 3-methylbutane-1,2-diol, and mixtures thereof, preferably from 1,2-propanediol, 1,3-propanediol, 1,3-butanediol, 2-methyl-1,3-propanediol, 1,2,3-propanetriol, and mixtures thereof; with preferably said at least one glycolic solvent being 1,3-propanediol.

Preferably, the composition according to the invention is such that:
i) the water/glycol solvent weight ratio is (depending on the nature of the glycol) between 98/2 and 20/80, preferably between 80/20 and 20/80, advantageously between 80/20 and 50/50, and/or
ii) the pH of said composition is between about 4 and about 6 (for example between 4 and 6);
with preferably, said composition presenting characteristics i) and ii).

The applicant's works have made it possible to highlight the fact that the aforementioned parameters/operating conditions i) and ii) made it possible to obtain a hydroglycolic composition, namely a mixture of water and of at least one glycolic solvent, preferably a hydroglycolic solution, having optimal properties in terms of stability, bioavailability and biological activity of the organic silicon that it contains.

Advantageously, the composition according to the invention is such that said organo-silanol(s) stabilising/complexing agent is a biologically active substance (e.g. a physiologically active substance), preferably selected from adenosine, glycyrrhizic acid and/or its salts, glycyrrhizin and/or its salts, lactobionic acid and/or its salts, alginic acid and/or its salts, hyaluronic acid and/or its salts, lactose, trehalose, 6-deoxy-L-mannopyranose and/or its salts, theophylline acetic acid, ascorbic acid, lactic acid, salicylic acid and/or its salts, pyrrolidone carboxylic acid and/or its salts, arginine, serine, lysine and/or their salts, methionine and/or its salts, acetyl methionine, threonine, hydroxyproline, N-acetyl tyrosine, aspartic acid, glutamic acid and/or their salts, oleic alcohol, panthenol, caffeine, pectin, acefylline, chondroitin sulfate and/or their salts, hydrolysed pearl, a protein hydrolysate of animal or plant origin, for example a collagen hydrolysate of marine origin such as a collagen hydrolysate from fish skin(s), and mixtures thereof, advantageously chosen from alginic acid and/or its salts, 6-deoxy-L-mannopyranose and/or its salts, hyaluronic acid and/or its salts, ascorbic acid, hydroxyproline, theophylline acetic acid, salicylic acid and/or its salts, adenosine, caffeine, and mixtures thereof. Particularly preferably, said biologically active substance is alginic acid and/or its salts, or hyaluronic acid and/or its salts, or a mixture of alginic acid (and/or its salts) and hyaluronic acid (and/or its salts). In connection with the above-mentioned biologically active substances, they may be notably defined by a registration number on a database, such as the database of the "Chemical Abstracts Service" division (CAS). Thus, as an example of alginic acid and/or its salts, we can mention alginic acid (CAS no.:9005-32-7) as well as the sodium, potassium and calcium salts of alginic acid (respective CAS no.: 9005-38-3, 9005-36-1, 9005-35-0). As an example of hyaluronic acid and/or its salts, we can mention a high molecular weight hyaluronic acid (>1400 kDa) and a low molecular weight hyaluronic acid (<700 kDa), in particular in the form of sodium salts.

The fact that the organo-silanol(s) stabilising/complexing agent is a biologically active substance has the double advantage of allowing stabilisation of the above-mentioned first and second organo-silanols, notably via the formation of the ternary complex of the above-mentioned schema, which corresponds to its "primary function", but also of having one or more biological action(s) (for example physiological) on the body.

The invention also relates to a pharmaceutical composition, a drug for human or veterinary use, a medical device such as an injectable solution, a food supplement for human or animal use, a cosmetic composition, a dermocosmetic composition, comprising (or consisting essentially of) a composition according to the invention. Another object of the invention relates to a composition according to the invention for its use as a drug for human or veterinary use (preferably for human use).

The invention also relates to a composition according to the invention for its use in the prevention and/or limitation of skin damage related to skin ageing, in particular related to oxidative stress (ultraviolet radiation, atmospheric pollution, contact with chemical xenobiotics, etc.) that generate free radicals or reactive oxygen species, to boost epidermal, dermal and hypodermic cellular activity, and/or as a stimulant agent on the expression of fibrillar collagens and proteoglycans constituting the dermal-epidermal junction (namely for stimulating the expression of fibrillar collagens and proteoglycans constituting the dermal-epidermal junction), and/or as an agent suitable for reducing the size and/or visibility of noticeable skin pores associated with age. The invention therefore also relates to the use of a composition according to the invention, as defined within the present patent application, for reducing the size and/or visibility of noticeable skin pores associated with age. According to a particular embodiment of the invention with respect to such an action on skin pores, said organo-silanol stabilising/complexing agent suitable for allowing the formation of a molecular complex with at least one organo-silanol is adenosine.

Another object of the invention is an organo-silanol of the following general formula (III):

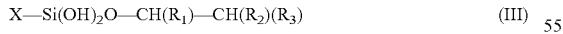

wherein:
the radical X is a linear or branched (advantageously linear) $C_1$-$C_4$ alkyl group, preferably $C_1$-$C_2$, possibly substituted with at least one hydroxyl group (preferably with one hydroxyl group), with preferably X being a methyl group;
$R_1$ is —H or —$CH_3$;
$R_2$ is —H, —OH, or —$CH_3$;
$R_3$ is —$CH_3$, —$CH_2$—$CH_3$, —$CH_2OH$, —$CH(CH_3)$OH, —$CH_2$—$CH_2$—$CH_3$, —$CH_2$—$CH_2$—$CH_2$—$CH_3$, —$CH_2$—$CH_2$—$CH_2$—$CH_2$—OH, or —$C(CH_3)(CH_3)$—OH.

According to a particular embodiment, said organo-silanol of general formula (III) has the following general formula (V):

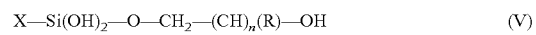

wherein:
the radical X is a linear or branched (advantageously linear) $C_1$-$C_4$ alkyl group, preferably $C_1$-$C_2$, possibly substituted with at least one hydroxyl group (preferably with one hydroxyl group), preferably X is a methyl group;
the radical R is a hydrogen atom or a $C_1$-$C_4$ alkyl group, in particular in $C_1$-$C_2$, preferably a hydrogen atom; and
n is a natural integer between 1 and 4, preferably between 1 and 3, with preferably n being 2.

According to another particular embodiment, said organo-silanol of general formula (III) is the reaction product of a mono-alkoxylation between one of the hydroxyl groups carried by the silicon atom of the organo-silanol of general formula (I), as defined above, and a glycolic solvent selected from 1,2-propanediol, 1,3-propanediol, 1,2-butanediol, 1,3-butanediol, 2-methyl-1,3-propanediol, 1,2,3-propanetriol, 1,2-hexanediol, 1,6-hexanediol, 1,2-dihydroxypentane, hexylene glycol, 3-methylbutane-1,2-diol, and mixtures thereof, preferably 1,2-propanediol, 1,3-propanediol, 1,3-butanediol, 2-methyl-1,3-propanediol, 1,2,3-propanetriol, and mixtures thereof.

Preferably, said above-mentioned organo-silanol compound of general formula (III) is such that X is a methyl group, $R_1$ is a hydrogen atom, $R_2$ is a hydrogen atom, and $R_3$ is —$CH_2$—OH.

Said organo-silanol is (3-hydroxypropoxy)-(methyl)silanediol. As indicated above, the compound displays a chemical shift at $\delta = -39.1$ ppm in liquid $^{29}$Si NMR spectroscopy.

Another object of the invention relates to a process for preparing an organo-silanol of the above-mentioned general formula (III), comprising the following steps:
a) obtaining an organo-silanol of the following general formula (I):

wherein the radical X is a linear or branched (advantageously linear) $C_1$-$C_4$ alkyl group, preferably $C_1$-$C_2$, possibly substituted with at least one hydroxyl group (preferably with one hydroxyl group), with preferably X being a methyl group;
b) contacting said organo-silanol of general formula (I) with at least one glycolic solvent corresponding to the following general formula (II):

wherein:
$R_1$ is —H or —$CH_3$;
$R_2$ is —H, —OH, or —$CH_3$;
$R_3$ is —$CH_3$, —$CH_2$—$CH_3$, —$CH_2OH$, —$CH(CH_3)$OH, —$CH_2$—$CH_2$—$CH_3$, —$CH_2$—$CH_2$—$CH_2$—$CH_3$, —$CH_2$—$CH_2$—$CH_2$—$CH_2$—OH, or —$C(CH_3)(CH_3)$—OH for a sufficient period of time to obtain, via a mono-alkoxylation reaction, the formation of the above-mentioned organo-silanol of general formula (III).

This preparation process is illustrated in particular by test 1 below as stated above, but also by test 7 below which concerns, separately from test 1, other organo-silanols of general formula (I) than methylsilanetriol and/or other stabilising/complexing agents than adenosine and/or other glycolic solvents of general formula (II) than 1,3-propanediol. For all these other illustrations of a hydroglycolic composition according to the invention, the presence of the above said organo-silanols of general formula (I) and of general formula (III) was confirmed in (liquid) $^{29}$Si NMR spectroscopy by the observation, on each control spectrum, of two singlets of distinct intensity but of chemical shifts (δ) very close to the indicative values of minus 39.1 ppm (δ=−39.1 ppm) and minus 38.6 ppm (δ=−38.6 ppm), which were primarily and specifically recorded for the organic silicon in hydroglycolic solution, under test 1, the difference in chemical shift (Δδ) between the two singlets being dependent on the nature of the silylated reagents leading to the organo-silanol of general formula (I) as well as on the nature of the glycolic solvent of formula (II), both involved in the formation of the new —Si—O—C— covalent bond [see test 7 below].

The invention also relates to the use of an organo-silanol according to the general formula (III) for increasing the stability of a composition/system comprising:

an organo-silanol of the following general formula (I):

$$X\text{—Si(OH)}_3 \quad (I)$$

wherein the radical X is a linear or branched (advantageously linear) $C_1$-$C_4$ alkyl group, preferably $C_1$-$C_2$, possibly substituted with at least one hydroxyl group (preferably with one hydroxyl group), with preferably X being a methyl group; and an organo-silanol(s) stabilising agent as defined above.

The invention also extends to a composition, preferably cosmetic or dermocosmetic, intended to prevent and/or repair skin damage associated with age. This composition comprises, in association with any excipient physiologically compatible with skin, as the main active ingredient, a composition according to the invention, and in particular a hydroglycolic composition according to the invention, preferably in the form of a hydroglycolic solution, as defined above. Said composition, preferably cosmetic or dermocosmetic, is suitable for topical cutaneous administration, and presented in all the forms normally used for such administration. By way of example and non-exhaustively, the compositions may be in the form of suspensions, lotions, creams, aqueous or hydroalcoholic gels, powders and multiple emulsions which may possibly be microemulsions or nanoemulsions, etc. Said composition, preferably cosmetic or dermocosmetic, may contain, as an excipient compatible with skin, at least one excipient known to the person skilled in the art and acceptable in the cosmetic or dermocosmetic fields, chosen from oils, waxes, silicone elastomers, surfactants, co-surfactants, thickeners and/or gelling agents, humectants, emollients, organic or inorganic sunscreens, photostabilisers, preservatives with the exception of aldehyde-donor preservatives, colouring agents, mattifying agents, fats, pigments, tensing agents, sequestrants, perfumes, etc., and mixtures thereof. Said composition, preferably cosmetic or dermocosmetic, may further comprise one or more additional active ingredients chosen—without this list being limitative—from deglycating agents, agents stimulating collagen or elastin synthesis or preventing their degradation, agents stimulating glycosaminoglycan or proteoglycan synthesis or preventing their degradation, agents increasing cell proliferation, depigmenting or pro-pigmenting agents, anti-oxidant or anti-radical or anti-pollution agents, moisturizing agents, agents stimulating lipolysis, draining or detoxifying agents, anti-inflammatory agents, penetration accelerating agents, desquamating agents, soothing and/or anti-irritating agents, astringent agents, agents acting on microcirculation, etc., and mixtures thereof.

Furthermore, another object of the invention is the use of the composition according to the invention, and in particular a hydroglycolic composition according to the invention, preferably in the form of a hydroglycolic solution, as a cosmetic or dermocosmetic active ingredient, or for the manufacture of food, dietetic, cosmetic or pharmaceutical preparations or supplements for human or animal use. Advantageously, the composition according to the invention in the above compositions, preparations, medical devices or supplements is between 1% and 15% (for example between 1% and 10%) by weight out of the total weight of the above composition, preparation, medical device or supplement, preferably between 3% and 8% (for example between 3% and 7%) by weight.

Definitions

"Organic silicon" must be taken to mean one or more organo-silanol compounds.

"Organo-silanol(s) stabilising/complexing agent" (sometimes abbreviated within the present application as "stabilising/complexing agent" or simply referred to as "organo-silanol(s) stabilising agent", for the sake of conciseness), must be taken to mean a molecule, a compound, a substance or an entity suitable for allowing the formation of a molecular complex with at least one organo-silanol via the establishment of at least one weak chemical bond, preferably at least one hydrogen bond, with said at least one organo-silanol.

"Hydrogen bonds" must be taken to mean hydrogen bonds as defined by the International Union of Pure and Applied Chemistry in its recommendations (Arunan E. et al., Pure Appl. Chem., 2011, vol. 83, pp. 1637-1641).

"Stable" or "stability over time" must be taken to mean a stability of the organic silicon in solution for at least 9 months without any observed opalescence.

"Bioavailability" must be taken to mean the ability of a molecule to be absorbed and distributed in the body. For example, in the case of topical cutaneous administration, bioavailability means the ability to penetrate the stratum corneum to the deepest layers of the skin (epidermis, dermis, hypodermis).

"Biologically active" or "biologically active" refers to the property of a molecule, a substance, a compound or an entity to present biological action/activity, i.e. its introduction into living organisms will result in a reaction by the latter (which may be beneficial or harmful). It goes without saying that, in the context of the present invention, the sought biological action/activity is "beneficial" in nature.

DETAILED DESCRIPTION

The following detailed description is intended to set out the invention in a sufficiently clear and complete manner, notably using examples, but should in no way be considered as limiting the scope of protection to the particular embodiments and examples presented hereafter.

EXAMPLES

Test 1: Process for Preparing an Organic Silicon in Hydroglycolic Solution According to the Invention (Namely the Above-Mentioned "Ternary Complex Represented by the Scheme OS(I)-AS-OS(III)") Involving the Substances Methylsilanetriol and (3-Hydroxypropoxy)-(Methyl)Silanediol as Well as Adenosine as a Stabilising/Complexing Agent First, 8.55 g of adenosine (32 mmoles) is suspended in approximately 320 g of water. Then, 6.92 g of a commercial solution of sodium methylsiliconate (equivalent to 32 mmoles of methylsilanetriol), previously diluted in approx. 40 ml of water, are added to the previous suspension. The resulting pH is adjusted to 4.95 using a few drops of 1N HCl. 500 g of 1,3-propanediol are then introduced with stirring at room temperature. The mass of solution is finally adjusted to 1 kg by adding water. The resulting complex solution (in a water/1,3-propanediol 50/50 weight ratio) is finally adjusted to a pH of 5 using a few drops of 1N HCl. A clear, colourless and odourless solution is obtained.

Test 2: Skin Penetration Profile for Organic Silicon in Hydroglycolic Solution

Principle: the skin epidermis is composed of four layers from the most superficial one ("stratum corneum") to the deepest one ("basal layer"). For a structurally defined organic entity, it is thus possible to determine its octanol/buffer partition coefficient ("Log P"), enabling:

the determination of the skin permeability constant ("Kp") from the so-called "Potts & Guy" model equation (according to the article "Predicting skin permeability") (Potts R. O. & Guy R. H., Pharm. Res., 1992, vol. 9, pp. 663-669);

and thus making it possible to express for the targeted entity its ability to cross the epidermal skin barrier (Arct J. et al., SOFW J., 2003, vol. 129, pp. 2-9).

In the case of the present invention, a theoretical determination of Log P was carried out using the "Chemdraw®" prediction software marketed by the company "Cambridge soft", for the two following cases:

case 1: methylsilanetriol associated and stabilised, in exclusively aqueous solution, by a stabilising/complexing agent (weak bonds)

case 2: organic silicon in hydroglycolic solution (water/glycol: 50/50) according to the invention (namely the above-mentioned "ternary complex represented by the scheme OS(I)-AS-OS(III)") involving the substances methylsilanetriol, (3-hydroxypropoxy)-(methyl)silanediol, and a stabilising/complexing agent.

The results are collated in table 1 below:

TABLE 1

| Organic silicon | Log P | Kp (cm · h$^{-1}$) · 10$^{-5}$ |
| --- | --- | --- |
| Case 1 | −1.30 | 5.8 |
| Case 2 (according to the invention) | −0.71 | 6.7 |

Considering that the flux (i.e. the quantity of solute which passes into skin per unit area) is proportional to "Kp" and that the higher the "Kp" the more the product penetrates, the results above evidence a higher permeability constant for the composition according to the invention. It is therefore predicted that such a composition ("ternary complex") has a greater ability to cross the epidermal skin barrier and therefore a greater bioavailability than, for example, a methylsilanetriol belonging to the state of the art and stabilised by weak bonds (hydrogen bonds).

Test 3: Discovering the Stability Over Time of an Organic Silicon in Hydroglycolic Solution Principle: the stability of methylsilanetriol complexes with various metallic elements of the periodic table, in an acidic medium, is known and has been studied (Vevere I. et al., Latvijas Ķīmijas Žurnāls, 1996, vol. 1, pp. 70-73, and references cited). The aim is to observe the appearance of insoluble species in aqueous solution, which, under an incident and reflected light beam, are visually expressed by a blue opalescence of the solution.

The same stability study as the one from the state of the art was therefore conducted, for the two following cases:

case 1: methylsilanetriol complex associated and stabilised, in exclusively aqueous solution, by weak bonds (hydrogen bonds) with ascorbic acid case 2: organic silicon in hydroglycolic solution (water/glycol: 50/50) according to the invention (namely the above-mentioned "ternary complex represented by the scheme OS(I)-AS-OS(III)") involving the substances methylsilanetriol and (3-hydroxypropoxy)-(methyl)silanediol, as well as the same stabilising/complexing agent from case 1

The results are collated in table 2 below:

TABLE 2

| | Maximum stability | |
| --- | --- | --- |
| Organic silicon | pH | T (days) |
| Case 1 | 4.0-5.0 | 110 |
| Case 2 (according to the invention) | 5.0-6.0 | 551 |

The results underline a much higher stability of an organic silicon in hydroglycolic solution according to the invention than of the same organic silicon but without a glycolic compound in solution.

Test 4: Discovering the Cytostimulant Effect of an Organic Silicon in Hydroglycolic Solution on Reconstructed Epidermis of Human Origin The culturing of the RHE consisted in placing them in an "MCDB 153" growth medium (supplier: SkinEthic®) containing 5 mg/mL of insulin, 1.5 mM of $CaCl_2$ and 25 mg/mL of gentamycin, for 24 hours at 37° C. and 5% $CO_2$.

The cell proliferation is observed by the immunostaining technique (Gerdes et al., Int. J. Cancer (1983), vol. 31, pp. 13-20) by using the cell proliferation marker "Ki67", for the three following configurations (after twice-daily deposition of 100 μl on the RHE):

case 1: PBS buffer solution (control)

case 2: methylsilanetriol complex associated and stabilised, in exclusively aqueous solution, by weak (hydrogen) bonds with alginic acid case 3: organic silicon in hydroglycolic solution (water/glycol: 50/50) according to the invention (namely the above-mentioned "ternary complex represented by the scheme OS(I)-AS-OS(III)") involving the substances methylsilanetriol and (3-hydroxypropoxy)-(methyl)silanediol as well as the same stabilising/complexing agent from case 2

The results obtained are collated in table 3 below:

TABLE 3

| Organic silicon | Concentration (%) | % cells expressing Ki67/ total number of cells (% compared to the control) |
| --- | --- | --- |
| Case 1 (control) | — | — |
| Case 2 | 5 | +35 ± 0.5 |
| Case 3 (according to the invention) | 5 | +58 ± 1 |

The results underline a potentiated cytostimulation for the organic silicon in hydroglycolic solution according to the invention, superior to that of the same organic silicon but devoid of a glycolic compound in solution.

Test 5: Determining and Discovering the Ability of an Organic Silicon in Hydroglycolic Solution According to the Invention to Limit the Endogenous Synthesis of an Intracellular Signalling Agent, Nitric Oxide (NO)

As a preamble, it is stated that nitric oxide is a free radical species involved in skin ageing mechanisms (Ahsanuddin S. et al., AIMS Molecular Sciences, 2016, vol. 3, pp. 187-195). Then experimentally, the test was performed on murine macrophages of cell line "RAW 264.7". These macrophages were cultured in a complete culture medium "DMEM" (with 4.5 g/l of glucose and 10% foetal calf serum (FCS)), then kept in an atmosphere of 37° C. and 5% $CO_2$. On D-1, the macrophages were seeded in 24-well plates at 65789 cells/$cm^2$. At D0+2 hours, the macrophages were then stressed by the application of lipopolysaccharides (LPS), inducing the production of nitric oxide (LPS at 10 ng/ml), and then incubated at 37° C. and 5% $CO_2$ for a further 22 hours still in the presence of the treatments. On D+1, the culture supernatants were harvested for nitric oxide/nitrites quantification (Griess Reagent Kit for nitrite quantitation, Invitrogen, reference G7921) and statistical analysis in triplicate or quadriplicate (depending on the complex), at 540 nm absorbance, for the five following configurations:

case 1: control with LPS stress (abbreviation "LPS-stress")

case 2: methylsilanetriol complex associated and stabilised, in exclusively aqueous solution, by weak (hydrogen) bonds with hydroxyproline case 3: organic silicon in hydroglycolic solution (water/glycol: 50/50) according to the invention (namely the above-mentioned "ternary complex represented by the scheme OS(I)-AS-OS(III)") involving the substances methylsilanetriol and (3-hydroxypropoxy)-(methyl)silanediol as well as the same stabilising/complexing agent from case 2 case 4: methylsilanetriol complex associated and stabilised, in exclusively aqueous solution, by weak (hydrogen) bonds with 6-deoxy-L-mannopyranose case 5: organic silicon in hydroglycolic solution (water/glycol: 50/50) according to the invention (namely the above-mentioned "ternary complex represented by the scheme OS(I)-AS-OS(III)") involving the substances methylsilanetriol and (3-hydroxypropoxy)-(methyl)silanediol as well as the same stabilising/complexing agent from case 4.

Similarly to the above-mentioned tests 2 and 4, the present test allows a comparison, for a same concentration, of an in vitro biological behaviour between an associated and stabilised methylsilanetriol complex in exclusively aqueous solution, and the same associated and stabilised methylsilanetriol complex but in hydroglycolic solution.

The results are collated in table 4 below, notably expressed as % inhibition of nitric oxide secretion compared to the untreated control.

TABLE 4

| Compound | Secreted quantity of NO (% LPS) | % inhibition of NO secretion |
|---|---|---|
| Case 1 - Control ("LPS-stress") | 100 | N/A |
| Case 2 - "LPS-stress" + organic silicon at 0.5% conc. | 75 | −25% |
| Case 3 - "LPS-stress" + organic silicon at 0.5% conc. | 55 | −45% |
| Case 4 - "LPS-stress" + organic silicon at 0.25% conc. | 74 | −26% |
| Case 5 - "LPS-stress" + organic silicon at 0.25% conc. | 62 | −38% |

The results underline an inhibition of nitric oxide production induced by LPS stress potentiated for organic silicon in hydroglycolic solution according to the invention, greater than that of the same organic silicon but without a glycolic compound in solution.

Test 6: Determining and Discovering the Ability of an Organic Silicon in Hydroglycolic Solution According to the Invention to Limit the Production of a Lipid Mediator, Prostaglandin $E_2$ (PGE2)

As a preamble, it is stated that prostaglandin $E_2$ (PGE2) is a marker in particular designated for studying the effects of ageing on type I collagen production (Shim J. H, Int. J. Mol. Sc., 2019, vol. 20, 5555, pp. 1-12). Then experimentally, the test was performed under the same conditions as test 5 above, i.e. the same macrophage line and the same culturing, except for the following step: on D+1, the culture supernatants were harvested in order to perform quantification of secreted PGE2 (Prostaglandin $E_2$ Parameter Assay Kit, reference KGE004B, R&D System) and a statistical analysis in triplicate, at 450 nm absorbance, the three tested configurations being:

case 1: control with stress (LPS-stress)

case 2: methylsilanetriol complex associated and stabilised, in exclusively aqueous solution, by weak (hydrogen) bonds with hyaluronic acid (<700 kDa)

case 3: organic silicon in hydroglycolic solution (water/glycol: 50/50) according to the invention (i.e. the above-mentioned "ternary complex represented by the scheme OS(I)-AS-OS(III)") involving the substances methylsilanetriol and (3-hydroxypropoxy)-(methyl)silanediol as well as the same stabilising/complexing agent from case 2 case 4: methylsilanetriol complex associated and stabilised, in exclusively aqueous solution, by weak (hydrogen) bonds with 6-deoxy-L-mannopyranose case 5: organic silicon in hydroglycolic solution (water/glycol: 50/50) according to the invention (i.e. the above-mentioned "ternary complex represented by the scheme OS(I)-AS-OS(III)") involving the substances methylsilanetriol and (3-hydroxypropoxy)-(methyl)silanediol as well as the same stabilising/complexing agent from case 4.

Similarly to the above-mentioned tests 2 to 5, the present test allows a comparison, for the same concentration, of an in vitro biological behaviour between an associated and stabilised methylsilanetriol complex in exclusively aqueous solution and the same associated and stabilised methylsilanetriol complex but in hydroglycolic solution.

The results are collated in table 5 below, notably expressed as % inhibition of PGE2 secretion compared to the untreated control.

TABLE 5

| Compound | Secreted quantity of $PGE_2$ (% LPS) | % inhibition of $PGE_2$ secretion |
|---|---|---|
| Case 1 - Control ("LPS-stress") | 100 | N/A |
| Case 2 - "LPS-stress" + organic silicon at 0.25% conc. | 108 | N/A |
| Case 3 - "LPS-stress" + organic silicon at 0.25% conc. | 74 | −26% |
| Case 2 - "LPS-stress" + organic silicon at 0.5% conc. | 105 | N/A |
| Case 3 - "LPS-stress" + organic silicon at 0.5% conc. | 66 | −34% |
| Case 2 - "LPS-stress" + organic silicon at 1% conc. | 99 | −1% |
| Case 3 - "LPS-stress" + organic silicon at 1% conc. | 63 | −27% |
| Case 4 - "LPS-stress" + organic silicon at 0.25% conc. | 99 | −1% |
| Case 5 - "LPS-stress" + organic silicon at 0.25% conc. | 78 | −22% |

The results underline an inhibition of the PGE2 production induced by LPS stress, potentiated for organic silicon in hydroglycolic solution according to the invention, dose-dependent and superior to that of the same organic silicon but without a glycolic compound in solution.

Test 7: Process for Preparing an Organic Silicon in Hydroglycolic Solution According to the Invention (Namely the Above-Mentioned "Ternary Complex Represented by the Scheme OS(I)-AS-OS(III)") Involving Various Organo-Silanols of General Formula (I), Various Organo-Silanols of General Formula (III), Various Glycolic Solvents of General Formula (II), Various Water/Glycolic Solvent Weight Ratios, and Finally Various Stabilising/Complexing Agents Experimentally, the preparation processes for each of the illustrative examples below were carried out according to the chronology and operating conditions described in test 1 above. They led, in each of the 10 generated examples set out in table 6 below, to a clear, colourless and odourless solution, which was then analysed in $^{29}Si$ NMR spectroscopy using a "Brucker Avance 500" spectrometer under the following conditions:

analysis temperature: room temperature (300° K.)
relaxation time: 30 seconds
number of scans: 6000
analysis time: 50 hours
external reference: $D_2O$ (deuterated solvent)
NMR tube internal diameter: 10 mm
core: $^{29}Si$; frequency: 99.36 MHz; Pulse program: Zgig

TABLE 6

| | | Composition according to the invention [ternary, stabilised complex] OS(I) -- AS -- OS(III) | | |
|---|---|---|---|---|
| Silylated reagent Stabilising agent [AS] | Glycolic solvent of formula (II) HO—CH($R_1$)—CH($R_2$)($R_3$) $H_2O$/glycol weight ratio | OS(I) X—Si(OH)$_3$ [δ in ppm] Lot | OS(III) X—Si(OH)$_2$—O—CH(R1)—CH($R_2$)($R_3$) [δ in ppm] Lot | Δδ (ppm) |
| sodium methylsiliconate | $R_1$ = H $R_2$ = H $R_3$ = —CH$_2$OH | X = —CH$_3$ δ = −37.33 ppm | X = —CH$_3$ $R_1$ = H $R_2$ = H $R_3$ = —CH$_2$OH δ = −37.84 ppm | 0.51 |
| hyaluronic acid sodium methylsiliconate | 50/50 $R_1$ = H $R_2$ = CH$_3$ $R_3$ = —CH$_2$OH | E17384 X = —CH$_3$ δ = −37.46 ppm | E17384 X = —CH$_3$ $R_1$ = H $R_2$ = CH$_3$ $R_3$ = —CH$_2$OH δ = −38.05 ppm | 0.59 |
| hyaluronic acid sodium methylsiliconate | 50/50 $R_1$ = H $R_2$ = H $R_3$ = —CH(CH$_3$)OH | E17390 X = —CH$_3$ δ = −37.85 ppm | E17390 X = —CH$_3$ $R_1$ = H $R_2$ = H $R_3$ = —CH(CH$_3$)OH δ = −38.10 ppm | 0.25 |
| hyaluronic acid sodium methylsiliconate | 50/50 $R_1$ = H $R_2$ = H $R_3$ = —CH$_2$OH | E17385 X = —CH$_3$ δ = −37.34 ppm | E17385 X = —CH$_3$ $R_1$ = H $R_2$ = H $R_3$ = —CH$_2$OH δ = −37.85 ppm | 0.51 |
| alginic acid sodium methylsiliconate | 50/50 $R_1$ = H $R_2$ = H $R_3$ = —CH$_2$OH | E17386 X = —CH$_3$ δ = −37.33 ppm | E17386 X = —CH$_3$ $R_1$ = H $R_2$ = H $R_3$ = —CH$_2$OH δ = −37.85 ppm | 0.52 |
| 6-deoxy-L-mannopyranose sodium methylsiliconate | 50/50 $R_1$ = H $R_2$ = OH $R_3$ = —CH$_2$OH | E17387 X = —CH$_3$ δ = −37.26 ppm | E17387 X = —CH$_3$ $R_1$ = H $R_2$ = OH $R_3$ = —CH$_2$OH δ = −37.56 ppm | 0.30 |

TABLE 6-continued

| Silylated reagent Stabilising agent [AS] | Glycolic solvent of formula (II) HO—CH($R_1$)—CH($R_2$)($R_3$) $H_2O$/glycol weight ratio | Composition according to the invention [ternary, stabilised complex] OS(I) -- AS -- OS(III) | | |
|---|---|---|---|---|
| | | OS(I) X—Si(OH)$_3$ [δ in ppm] Lot | OS(III) X—Si(OH)$_2$—O—CH(R1)—CH($R_2$)($R_3$) [δ in ppm] Lot | Δδ (ppm) |
| 6-deoxy-L-mannopyranose sodium methylsiliconate | 30/70 $R_1$ = H $R_2$ = OH $R_3$ = —CH$_2$OH | E17483 X = —CH$_3$ δ = −37.00 ppm | E17483 X = —CH$_3$ $R_1$ = H $R_2$ = OH $R_3$ = —CH$_2$OH δ = −37.28 ppm | 0.28 |
| theophylline acetic acid sodium methylsiliconate | 50/50 $R_1$ = H $R_2$ = H $R_3$ = —CH$_2$OH | E17482 X = —CH$_3$ δ = −37.33 ppm | E17482 X = —CH$_3$ $R_1$ = H $R_2$ = H $R_3$ = —CH$_2$OH δ = −37.84 ppm | 0.51 |
| hydroxyproline butyltrichlorosilane | 50/50 $R_1$ = H $R_2$ = H $R_3$ = —CH$_2$OH | E17388 X = —CH$_2$—CH$_2$—CH$_2$—CH$_3$ δ = −38.24 ppm | E17388 X = —CH$_2$—CH$_2$—CH$_2$—CH$_3$ $R_1$ = H $R_2$ = H $R_3$ = —CH$_2$OH δ = −39.14 ppm | 0.90 |
| lactic acid hydroxymethyltriethoxysilane | 50/50 $R_1$ = H $R_2$ = H $R_3$ = —CH$_2$OH | E38480 X = —CH$_2$OH δ = −47.93 ppm | E38480 X = —CH$_2$OH $R_1$ = H $R_2$ = H $R_3$ = —CH$_2$OH δ = −49.08 ppm | 1.15 |
| caffeine | 50/50 | E38478 | E38478 | |

Finally, by way of final illustrations, we mention below five examples of formulations of compositions according to the invention containing an organic silicon in hydroglycolic solution which is the object of the aforementioned invention, together with a description used for the preparation of each formulated organic silicon.

Formula A (Cream)

Organic silicon in hydroglycolic solution (water/1,3-propanediol; 50/50) according to the invention (namely the above-mentioned "ternary complex represented by the scheme OS(I)-AS-OS(III)") involving the substances methylsilanetriol, (3-hydroxypropoxy)-(methyl)silanediol and adenosine as a stabilising/complexing agent, said organic silicon in

| hydroglycolic solution being prepared according to test 1 described above | 5% |
|---|---|
| Hydrogenated polyisobutene | 7% |
| Isobutyl myristate | 3% |
| Cetyl palmitate | 7% |
| Ethylene glycol monostearate | 5% |
| Sorbitan laurate | 2% |
| Polysorbate 20 | 2% |
| Carbomer (copolymer of acrylate/acrylamide & mineral oil) | 0.3% |
| Phenoxyethanol | 0.5% |
| Water | qsp 100% |

Formula B (Gel)

Organic silicon in hydroglycolic solution (water/1,3-propanediol; 80/20) according to the invention (namely the above-mentioned "ternary complex represented by the scheme OS(I)-AS-OS(III)") involving the substances methylsilanetriol, (3-hydroxypropoxy)-(methyl)silanediol and N-acetyl-tyrosine as a stabilising/complexing agent, said organic silicon in hydroglycolic solution being prepared according to the preparation process described in test 1 above, but using successively 7.1 g of N-acetyl-tyrosine (32 mmoles) in 690 g of $H_2O$, 6.92 g of a commercial solution of sodium methylsiliconate (equivalent to 32 mmoles of methylsilanetriol) diluted in 40 g of water, 200 g of 1,3-propanediol and then

| mass-adjustment by addition of $H_2O$ to 1 kg | 6% |
|---|---|
| Carbomer (copolymer of acrylate/acrylamide & mineral oil) | 1.5% |
| Sodium benzoate | 0.2% |
| Sorbic acid | 1% |
| Soda | 0.13% |
| Phenoxyethanol | 0.9% |
| Water | qsp 100% |

Formula C (Lotion)

Organic silicon in hydroglycolic solution (water/1,3-butanediol; 50/50) according to the invention (namely the above-mentioned "ternary complex represented by the scheme OS(I)-AS-OS(III)") involving the substances methylsilanetriol, (2-methyl-3-hydroxypropoxy)-(methyl)silanediol and trehalose as a stabilising/complexing agent, said organic silicon in hydroglycolic solution being prepared according to the preparation process described in test 1 above, but using successively 50 g of trehalose (146 mmoles) in 690 g of $H_2O$, 6.92 g of a commercial solution of sodium methylsiliconate (equivalent to 32 mmoles of methylsilanetriol) diluted in 40 g of water, 500 g of 1,3-butanediol and then

| | |
|---|---|
| mass-adjusted by addition of H$_2$O to 1 kg | 3% |
| Chlorphenesin | 0.2% |
| Phenonip (parabens - butyl, ethyl, isobutyl, methyl, propyl parahydroxybenzoate and phenoxyethanol) | 0.6% |
| Xanthan gum | 0.3% |
| Triethanolamine | 0.03% |
| Water | qsp 100% |

Formula D (Emulsion)

Organic silicon in hydroglycolic solution (water/1,2,3-propanetriol; 30/70) according to the invention (namely the above-mentioned "ternary complex represented by the scheme OS(I)-AS-OS(III)") involving the substances methylsilanetriol, (2,3-dihydroxypropoxy)-(methyl)silanediol and L-arginine HCl as a stabilising/complexing agent, said organic silicon in hydroglycolic solution being prepared according to the preparation process described in test 1 above, but using successively 6.7 g of L-arginine HCl (32 mmoles), 6.92 g of a commercial solution of sodium methylsiliconate (equivalent to 32 mmoles of methylsilanetriol) diluted in 40 g of water, 700 g of 1,2,3-propanetriol and then

| | |
|---|---|
| mass-adjustment by addition of H$_2$O to 1 kg | 8% |
| Hydrogenated polydecene | 8% |
| Capric/caprylic triglycerides | 2% |
| Ethoxydiglycol oleate | 8% |
| Glyceryl stearate | 2% |
| Dimethicone | 1% |
| Polyethylene glycol-100 stearate and glyceryl stearate | 5% |
| Propyl paraben | 0.3% |
| Stearyl alcohol | 1% |
| EDTA (Ethylenediaminetetraacetic acid disodium dihydrate salt) | 0.2% |
| Xanthan gum | 0.4% |
| Wheat germ oil | 1% |
| Macadamia seed oil | 1% |
| Polyethylene glycol-8 & tocopherol & ascorbyl palmitate & ascorbic acid & citric acid | 0.07% |
| Triethanolamine | 0.35% |
| Water | qsp 100% |

Formula E (Food Supplement)

Organic silicon in hydroglycolic solution (water/1,2,3-propanetriol; 80/20) according to the invention (namely the above-mentioned "ternary complex represented by the scheme OS(I)-AS-OS(III)") involving the substances methylsilanetriol, (2,3-dihydroxypropoxy)-(methyl)silanediol and alginic acid as a stabilising/complexing agent, said organic silicon in hydroglycolic solution being prepared according to the preparation process described in test 1 above, but using successively 3.9 g of alginic acid (18 mmoles), 6.92 g of a commercial solution of sodium methylsiliconate (equivalent to 32 mmoles of methylsilanetriol) diluted in 40 g of water, 200 g of 1,2,3-propanetriol and then

| | |
|---|---|
| mass-adjustment by addition of H$_2$O up to 1 kg | 14% |
| Potassium sorbate | 0.05% |
| Sodium benzoate | 0.1% |
| Flavourings | 0.03% |
| Water | qsp 100% |

The invention claimed is:

1. A hydroglycolic solution comprising:
   a) a first organo-silanol of the following general formula (I):

$$X\text{—}Si(OH)_3 \qquad (I)$$

wherein X is a linear or branched C$_1$-C$_4$ alkyl group, optionally substituted with at least one hydroxyl group;

b) a second organo-silanol of the following formula (III):

$$X\text{—}Si(OH)_2\text{—}O\text{—}CH(R_1)\text{—}CH(R_2)(R_3) \qquad (III)$$

wherein:
   the X is a linear or branched C$_1$-C$_4$ alkyl group optionally substituted with at least one hydroxyl group;
   R$_1$ is —H or —CH$_3$;
   R$_2$ is —H, —OH, or —CH$_3$;
   R$_3$ is —CH$_3$, —CH$_2$—CH$_3$, —CH$_2$OH, —CH(CH$_3$)OH, —CH$_2$—CH$_2$—CH$_3$, —CH$_2$—CH$_2$—CH$_2$—CH$_3$, —CH$_2$—CH$_2$—CH$_2$—CH$_2$—OH, or —C(CH$_3$)(CH$_3$)—OH;

c) an organo-silanol(s) stabilising agent, suitable for allowing the formation of a molecular complex with said first and second organo-silanols via the establishment of at least one hydrogen bond with said first and second organo-silanols, wherein said organo-silanol(s) stabilising agent is selected from adenosine, glycyrrhizic acid and/or its salts, glycyrrhizin and/or its salts, lactobionic acid and/or its salts, alginic acid and/or its salts, hyaluronic acid and/or its salts, lactose, trehalose, 6-deoxy-L-mannopyranose and/or its salts, theophylline acetic acid, ascorbic acid, lactic acid, salicylic acid and/or its salts, pyrrolidone carboxylic acid and/or its salts, arginine and/or its salts, serine and/or its salts, lysine and/or its salts, methionine and/or its salts, acetyl methionine and/or its salts, threonine and/or its salts, hydroxyproline and/or its salts, N-acetyl tyrosine and/or its salts, aspartic acid and/or its salts, glutamic acid and/or its salts, oleic alcohol, panthenol, caffeine, pectin, acefylline, chondroitin sulfate, hydrolysed pearl, a protein hydrolysate of animal or plant origin, and mixtures thereof; and d) at least one glycolic solvent,
   wherein the water/glycolic solvent mass ratio is between 80/20 and 50/50.

2. The hydroglycolic solution of claim 1, wherein the molar ratio between said first organo-silanol and said second organo-silanol is between 100/1 and 100/20.

3. The hydroglycolic solution of claim 1, wherein said at least one glycolic solvent is of formula (II):

$$HO\text{—}CH(R_1)\text{—}CH(R_2)(R_3) \qquad (II)$$

wherein:
R$_1$ is —H or —CH$_3$;
R$_2$ is —H, —OH, or —CH$_3$; and,
R$_3$ is —CH$_3$, —CH$_2$—CH$_3$, —CH$_2$OH, —CH(CH$_3$)OH, —CH$_2$—CH$_2$—CH$_3$, —CH$_2$—CH$_2$—CH$_2$—CH$_3$, —CH$_2$—CH$_2$—CH$_2$—CH$_2$—OH, or —C(CH$_3$)(CH$_3$)—OH.

4. The hydroglycolic solution of claim 3, wherein:
the pH of said hydroglycolic solution is between about 4 and about 6.

5. The hydroglycolic solution of claim 1, wherein said second organo-silanol is of formula (III):

$$X\text{—}Si(OH)_2\text{—}O\text{—}CH(R_1)\text{—}CH(R_2)(R_3) \qquad (III)$$

wherein:
X is methyl;
R$_1$ is hydrogen;
R$_2$ is hydrogen; and
R$_3$ is —CH$_2$—OH.

6. A pharmaceutical composition comprising the hydroglycolic solution of claim 1, and a pharmaceutically acceptable excipient.

7. A cosmetic or dermocosmetic composition comprising the hydroglycolic solution of claim 1, and a cosmetically or dermocosmetically acceptable excipient.

8. The cosmetic or dermocosmetic composition of claim 7 for topical cutaneous administration.

9. The hydroglycolic solution of claim 1, wherein X in each instance is methyl.

10. The hydroglycolic solution of claim 2, wherein the molar ratio between said first organo-silanol and said second organo-silanol is between 100/10 and 100/15.

11. The hydroglycolic solution of claim 4, wherein said organo-silanol(s) stabilising agent is alginic acid and/or its salts, or hyaluronic acid and/or its salts.

12. The hydroglycolic solution of claim 1, wherein the protein hydrolysate of animal or plant origin is a collagen hydrolysate of marine origin.

13. The hydroglycolic solution of claim 12, wherein the collagen hydrolysate of marine origin is a collagen hydrolysate from fish skin(s).

* * * * *

UNITED STATES PATENT AND TRADEMARK OFFICE
CERTIFICATE OF CORRECTION

| | | |
|---|---|---|
| PATENT NO. | : 12,128,121 B2 | Page 1 of 1 |
| APPLICATION NO. | : 17/999321 | |
| DATED | : October 29, 2024 | |
| INVENTOR(S) | : Pierre Bondon | |

It is certified that error appears in the above-identified patent and that said Letters Patent is hereby corrected as shown below:

In the Claims

In Column 22, Line 22, Claim 1, delete "6-deoxy-L-mannopyranose and/or its salts," and insert -- 6-deoxy-L-mannopyranose, --, therefor.

Signed and Sealed this
Fourth Day of March, 2025

Coke Morgan Stewart
*Acting Director of the United States Patent and Trademark Office*